(12) United States Patent  (10) Patent No.: US 7,951,123 B2
Donovan et al.  (45) Date of Patent: May 31, 2011

(54) SPA WAX HEATING DEVICE

(75) Inventors: James A. Donovan, Tarpon Springs, FL (US); Tobi W. Ferguson, Lutz, FL (US)

(73) Assignee: James A. Donovan, Tarpon Springs, FL (US)

( * ) Notice: Subject to any disclaimer, the term of this patent is extended or adjusted under 35 U.S.C. 154(b) by 600 days.

(21) Appl. No.: 12/074,602

(22) Filed: Mar. 5, 2008

(65) Prior Publication Data

US 2009/0227967 A1   Sep. 10, 2009

(51) Int. Cl.
*A61M 35/00* (2006.01)
(52) U.S. Cl. .......................................... 604/292; 2/161.7
(58) Field of Classification Search .......... 604/290–292, 604/289; 2/161.7
See application file for complete search history.

(56) References Cited

U.S. PATENT DOCUMENTS

| 3,116,732 | A | * | 1/1964 | Cahill | 604/292 |
| 3,702,302 | A | * | 11/1972 | Wilson | 252/70 |
| 4,087,675 | A | * | 5/1978 | Sansonetti | 604/292 |
| 4,095,583 | A | * | 6/1978 | Petersen et al. | 126/263.07 |
| 4,171,340 | A | * | 10/1979 | Nishimura et al. | 422/36 |
| 5,035,003 | A | * | 7/1991 | Rinehart | 2/159 |
| 5,674,268 | A | * | 10/1997 | Riazi | 607/96 |
| 5,891,116 | A |   | 4/1999 | Mast | |
| 5,917,110 | A | * | 6/1999 | Kust | 71/27 |
| 5,984,953 | A | * | 11/1999 | Sabin et al. | 607/114 |
| 6,027,513 | A |   | 2/2000 | Massana Florensa | |
| 6,286,670 | B1 | * | 9/2001 | Smith | 206/221 |
| 6,547,063 | B1 | * | 4/2003 | Zaveri et al. | 206/219 |
| 6,627,072 | B1 |   | 9/2003 | Ridge | |
| 6,811,338 | B1 | * | 11/2004 | Manske, Jr. et al. | 401/7 |
| 6,905,487 | B2 | * | 6/2005 | Zimmerman | 604/292 |
| 6,914,168 | B2 |   | 7/2005 | Pilling et al. | |
| 7,021,848 | B1 | * | 4/2006 | Gruenbacher et al. | 401/1 |
| 2002/0017310 | A1 | * | 2/2002 | Gruenbacher et al. | 132/320 |
| 2003/0000517 | A1 | * | 1/2003 | Joseph et al. | 126/263.06 |
| 2003/0056276 | A1 | * | 3/2003 | Zimmerman | 2/159 |
| 2003/0101984 | A1 | * | 6/2003 | Li et al. | 126/263.05 |
| 2004/0022823 | A1 | * | 2/2004 | Uchida et al. | 424/401 |
| 2005/0000508 | A1 | * | 1/2005 | Schreft et al. | 126/263.09 |
| 2005/0048090 | A1 | * | 3/2005 | Rau | 424/401 |
| 2005/0258172 | A1 | * | 11/2005 | Gueret | 219/732 |
| 2006/0039685 | A1 | * | 2/2006 | Berrido et al. | 392/392 |
| 2007/0105977 | A1 | * | 5/2007 | Gabriel et al. | 523/122 |
| 2007/0117059 | A1 | * | 5/2007 | Goldenberg | 431/289 |
| 2007/0267583 | A1 | * | 11/2007 | Dodo | 250/493.1 |
| 2007/0289720 | A1 | * | 12/2007 | Sunol et al. | 165/80.5 |
| 2008/0097356 | A1 | * | 4/2008 | Donovan | 604/291 |
| 2008/0097357 | A1 | * | 4/2008 | Dononvan | 604/291 |
| 2008/0097358 | A1 | * | 4/2008 | Dovonan et al. | 604/291 |

(Continued)

FOREIGN PATENT DOCUMENTS

WO   WO 2006042294 A2 *   4/2006

*Primary Examiner* — Jacqueline F Stephens
*Assistant Examiner* — Paula L Craig
(74) *Attorney, Agent, or Firm* — Kinney & Lange, P.A.

(57) ABSTRACT

A wax heating device for wax treatment of human skin that includes a contained a controlled exothermic chemical reaction to melt wax on a flexible element for contacting human skin. A heating pouch contains a first portion. A heater element has an inner area with a first portion holding a heat generating material and a second portion holding an actuation agent, with a seal that is broken to actuate the heat generation and melt the wax.

9 Claims, 1 Drawing Sheet

U.S. PATENT DOCUMENTS

| | | | |
|---|---|---|---|
| 2008/0200971 A1* | 8/2008 | Dodo | 607/108 |
| 2009/0090349 A1* | 4/2009 | Donovan | 126/263.01 |
| 2009/0090351 A1* | 4/2009 | Sunol et al. | 126/263.08 |
| 2009/0151046 A1* | 6/2009 | Donovan | 2/174 |
| 2009/0151102 A1* | 6/2009 | Donovan | 15/208 |
| 2009/0277915 A1* | 11/2009 | Ferguson | 220/592.27 |
| 2009/0280043 A1* | 11/2009 | Ferguson | 422/236 |
| 2010/0047730 A1* | 2/2010 | Ferguson et al. | 432/9 |
| 2010/0065081 A1* | 3/2010 | Vracknos | 132/320 |

* cited by examiner

SPA WAX HEATING DEVICE

BACKGROUND

This invention relates to a spa wax heating device. More particularly, the invention relates to device for safely and efficiently melting spa wax in a glove for application of the wax to the skin.

The use of hot wax to treat or condition a person's hands is a known procedure often performed at spas and other personal care facilities, though a hot wax treatment can also be performed at home. After the wax solidifies, it is left in contact with the skin for a period of time of, for example, from five to thirty minutes.

U.S. Pat. No. 5,891,116 discloses one such hot wax skin treatment in which molten wax is placed in a glove and the hand is then inserted and the glove is massaged to spread the wax over all the skin. The wax is heated in a container and placed in the glove. The temperature is controlled by the composition of the wax, keeping the melting point at or below a safe temperature such as 39° to 55° C., with a preferred range of 42° to 50° C.

Another similar process is shown in U.S. Pat. No. 6,914,168, which applies paraffin to the skin by first melting the wax, placing an absorptive strip in the melted wax and transferring the wax to the person.

Other wax treatments are also known, such as the use of wax to remove hair or depilate areas of a person's skin. U.S. Pat. No. 6,027,513 discloses a case in which paraffin wax is heated, using a heating plate disposed in the case. Again the heat is external and not generated in place on the person being treated.

U.S. Pat. No. 6,627,072 describes the general use of paraffin waxes in SPA treatments and specifically covers a filter system for removing contaminants such as bacteria.

It would be a great advantage if a way of heating spa wax could be developed that have a controlled release of heat that is within acceptable safety limits.

Another advantage would be to provide a way of heating spa wax that is controlled and requires a specific action by the user such that the action is not one experienced by the glove or other device when carried about prior to use.

Yet another advantage would be to provide a way to generate heat by an exothermic reaction over a spa wax treating device quickly, without having to wait for an activation agent to make its way to all the reaction components.

Other advantages will appear hereinafter.

SUMMARY

It has now been discovered that the above and other objects of the present invention may be accomplished in the following manner. The unique aspect of this invention is that a controlled, dispersed exothermic reaction can be used to melt wax in situ both quickly and safely.

In it's simplest form the invention comprises a device such as a glove that is used to contact a person's skin and apply wax to the skin. A heating pouch is provided that melts the wax at an appropriate temperature once the heat element is activated. The wax is then dispersed inside the glove or other device.

The system inside the heating pouch contains an actuatable heat source comprising a heat generating material or materials that is separated from the actuation agent until needed. A seal maintains the separation of heat source and actuation agent. A frangible seal is preferred so that a simple flexing of the pouch breaks the seal and allows the heat generating material to be contacted by the actuation agent, generate heat and melt the wax. Any wax that is designed for contact with human skin may be used in this invention.

In the preferred embodiment, the heat generating materials are crystals that exotherm when contacted with a liquid actuating agent. The preferred actuation agent is water and the preferred heat generating material is crystalline calcium oxide. By spreading the crystals throughout the heater pouch, heat generating reactions take place in a large number of locations, thus heating the wax uniformly. A vacuum in the heater pouch increases the rate of flow of water to all regions of the pouch, causing uniform time of reaction. The amount of vacuum can range from about 8 psi to about 13 psi, with about 11 psi being preferred.

BRIEF DESCRIPTION OF THE DRAWINGS

For a more complete understanding of the invention, reference is hereby made to the drawings, in which.

DETAILED DESCRIPTION

Figure 1:
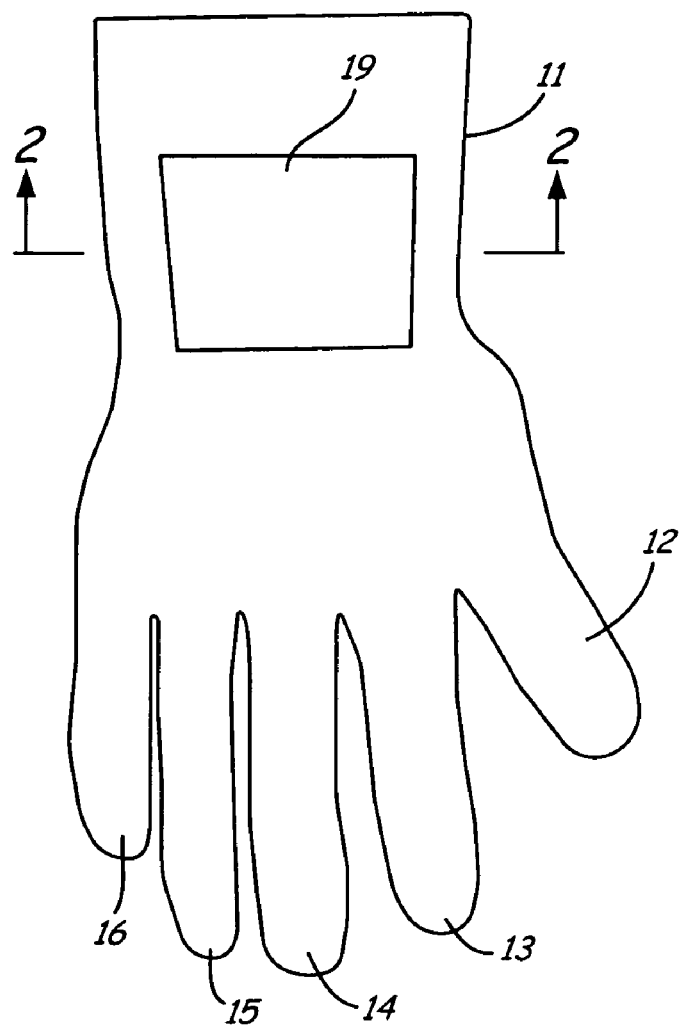
FIG. 1 is a side elevational view of one embodiment of the invention.
Figure 2:
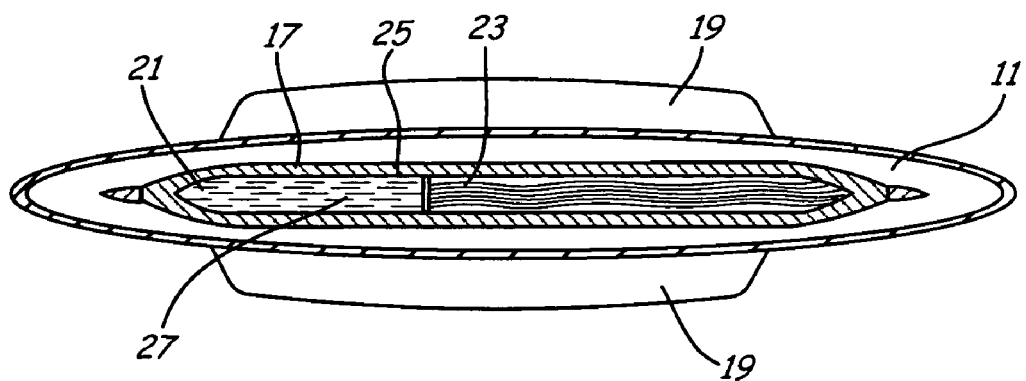
FIG. 2 is a sectional view taken along line 2-2 of FIG. 1.

As shown in FIG. 1, the device of this invention comprises a glove 11 with fingers 12, 13, 14, 15 and 16. Glove 11 also includes a pouch heater 17 for spa wax or paraffin 19 which, when the heater 17 is activated, will melt the wax 19 so that the user can insert his or her hand for a wax treatment.

Heater 17 made of a fluid impervious material such as a plastic. The inside 21 of heater 17 contains the heat generating materials 23 that exotherm when contacted by an actuating agent as described below. Heat generating materials 23 are preferably in crystal or granular form so that they can be spread throughout the inside 21 of pouch 17, thus, when activated, providing exotherm heat to the wax 19.

Preferred is an outer pouch 17 made from Aclar®, which is a polychlorotrifluoroethylene (PCTFE) material manufactured and sold by Honeywell International Inc. Aclar film is crystal clear, biochemically inert, chemical-resistant, non-flammable, and plasticizer- and stabilizer-free. Aclar laminates provide a wide range of gauges and thus barrier levels to allow flexibility in selecting the optimum barrier level for the chemical system chosen. Other similar pouch materials may be used as well. All that is required is that the material have a functional moisture and vapor barrier for the other components of the invention.

In order to have an uniform and even production of heat from the exotherms, it is preferred that the inside heat generating material 23 be at atmospheric pressure or 14.7 psi, and the inside 21 of the heater pouch 17 be under vacuum. Preferred pressures in 21 of pouch 17 are from about 8 psi to about 13 psi, with 10 or 11 psi being preferred. It is necessary to have a pressure differential sufficient to pull the activating agent 27 to the entire area where the heat generating material 23 has been placed. Too little or too great a pressure differential is not desired, for design and reliability reasons.

There are a number of combinations of heat generating materials and activating agents that are suitable for use in the present invention. The selection of specific components is to be based upon cost, compatibility, ease of control of the exotherm, and other factors.

The preferred activating material of this invention is water. This is plentiful and safe, and reacts with a number of materials to produce an exothermic reaction.

The preferred heat generating material is a crystal formed from several components that, when free from moisture, are stable for up to three to five years or more, and which react when moisture is present to generate heat. The preferred crystal is crystalline calcium oxide. The weight of the heat generating material to the volume of actuation agent ranges from about 1:2 to about 1:1, and preferably about 3:4. In the most preferred mixture of the heat generating material is a mixture of calcium oxide with the addition of a zeolite powder. Preferred is a ratio of calcium oxide to powdered zeolite is from about 14 to 20 for calcium oxide, and from about 7 to 10 for powdered zeolite. Most preferred is a ratio of calcium oxide to powdered zeolite is 2:1 and the ratio of the solids to the volume of water is about 3:4.

More than 150 zeolite types have been synthesized and 48 naturally occurring zeolites are known. They are basically hydrated alumino-silicate minerals with an "open" structure that can accommodate a wide variety of positive ions, such as Na+, K+, $Ca_2$+, $Mg_2$+ and others. These positive ions are rather loosely held and can readily be exchanged for others in a contact solution. Some of the more common mineral zeolites are: analcime, chabazite, heulandite, natrolite, phillipsite, and stilbite. An example mineral formula is: $Na_2Al_2Si_3O_{10}$-$16H_2O$.

The heat generation material most preferred, using the above components includes a calcined calcium oxide. This material is available as a small article size, with a diameter less than about 0.2 mm, and as a particle of somewhere between 0.2 and 0.8 mm. Larger particles are ground and smaller ones sieved, and the calcium oxide is then calcined. It has been found to be effective to calcine for at least 60 to 120 minutes, and preferably about 90 minutes, at temperatures above 500° C., and most preferably at about 550° C. for that period of time. The calcined calcium oxide is, of course, desiccated to prevent any contamination by moisture. Laboratory grade citric acid and powdered zeolite are mixed with the calcium oxide in moisture free conditions, in an appropriate reaction ratio to provide the exothermic reaction upon contact by the activating agent water.

The heat generating mixture 23 is spread throughout the inside 21 of heater pouch 17, obviously separated from the activating agent 27 by seal 25. The vacuum is then pulled to assist in dispersing the activating agent.

Any spa wax may be used as this is a commercially available product. Some examples of specific waxes used to treat human skin are disclosed in the previously mentioned U.S. Pat. Nos. 5,891,116 and 6,027,513, for example.

In a preferred embodiment, the heat generation material also includes a small quantity of polyalkyl glycol such as polyethylene glycol or similar materials which are used to coat the calcium oxide prior to initiating the exothermic reaction. This small coating, of 1% to 7% polyethylene glycol by weight in the total composition slows down the reaction with water to prolong the heat for over two hours. A preferred weight percent of polyethylene glycol is from 3% to 4%. Tests have been made that kept a container of one liter of water at a temperature of 140° F. for more than two hours. While this is a long time for a glove to remain hot, extending the reaction time at least for as long as needed to complete wax treatment is of considerable value.

Although the present invention has been described with reference to preferred embodiments, workers skilled in the art will recognize that changes may be made in form and detail without departing from the spirit and scope of the invention.

The invention claimed is:

1. A heatable personal wax treatment device, comprising:
   a flexible element for contacting human skin; and
   a quantity of personal treatment wax on the flexible element; and
   a heater unit positioned inside the personal treatment wax and having an inner area containing a heat generating material in a first portion and an actuation agent in a second portion,
   the heater unit further including a seal keeping the heat generating material from the actuation agent until actuation is desired;
   wherein the personal wax treatment device is a glove;
   and the breaking of the seal melts the personal treatment wax in situ.

2. The device of claim 1, wherein the first portion has an internal vacuum and second portion is at atmospheric pressure whereby breaking the seal causes a rapid mixing thereof.

3. The device of claim 1, wherein said actuation agent is a liquid and said heat generating material is a solid adapted to react with said actuation agent to cause an exothermic reaction.

4. The device of claim 3, wherein said actuation agent is water and said heat generating material is crystalline calcium oxide.

5. The device of claim 4, wherein said calcium oxide is calcined.

6. The device of claim 5, wherein the heat generating material further includes powdered zeolite admixed therein.

7. The device of claim 6, wherein the ratio of calcium oxide to powdered zeolite is from about 14 to 20 for calcium oxide and from about 7 to 10 for powdered zeolite.

8. The device of claim 7, wherein the ratio of calcium oxide to powdered zeolite is 2:1.

9. The device of claim 4, wherein the heat generating material includes a small quantity of polyalkyl glycol ranging from 1% to 7% by weight in the total composition.

* * * * *